(12) United States Patent
Ingmanson et al.

(10) Patent No.: US 8,157,151 B2
(45) Date of Patent: Apr. 17, 2012

(54) STAPLE LINE REINFORCEMENT FOR ANVIL AND CARTRIDGE

(75) Inventors: Michael D. Ingmanson, Stratford, CT (US); Sachin Shah, Milford, CT (US); Joseph McNellis, Bristol, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 370 days.

(21) Appl. No.: 12/579,605

(22) Filed: Oct. 15, 2009

(65) Prior Publication Data

US 2011/0089220 A1   Apr. 21, 2011

(51) Int. Cl.
*A61B 17/068* (2006.01)

(52) U.S. Cl. ............ 227/176.1; 227/19; 227/175.1; 606/151; 606/219

(58) Field of Classification Search ......... 227/19, 227/176.1, 175.1, 180.1, 178.1; 606/139, 606/151, 142, 219
See application file for complete search history.

(56) References Cited

U.S. PATENT DOCUMENTS

| | | |
|---|---|---|
| 3,054,406 A | 9/1962 | Usher |
| 3,124,136 A | 3/1964 | Usher |
| 4,347,847 A | 9/1982 | Usher |
| 4,354,628 A | 10/1982 | Green |
| 4,452,245 A | 6/1984 | Usher |
| 4,605,730 A | 8/1986 | Shalaby et al. |
| 4,655,221 A | 4/1987 | Devereux |
| 4,834,090 A | 5/1989 | Moore |
| 4,838,884 A | 6/1989 | Dumican et al. |
| 4,930,674 A | 6/1990 | Barak |
| 5,002,551 A | 3/1991 | Linsky et al. |
| 5,014,899 A | 5/1991 | Presty et al. |
| 5,040,715 A | 8/1991 | Green et al. |
| 5,065,929 A | 11/1991 | Schulze et al. |
| 5,205,459 A | 4/1993 | Brinkerhoff et al. |
| 5,263,629 A | 11/1993 | Trumbull et al. |
| 5,314,471 A | 5/1994 | Brauker et al. |
| 5,344,454 A | 9/1994 | Clarke et al. |
| 5,392,979 A | 2/1995 | Green et al. |
| 5,397,324 A | 3/1995 | Carroll et al. |
| 5,425,745 A | 6/1995 | Green et al. |
| 5,441,193 A | 8/1995 | Gravener |
| 5,441,507 A | 8/1995 | Wilk |
| 5,468,253 A | 11/1995 | Bezwada et al. |
| 5,503,638 A | 4/1996 | Cooper et al. |
| 5,542,594 A | 8/1996 | McKean et al. |
| 5,549,628 A | 8/1996 | Cooper et al. |

(Continued)

FOREIGN PATENT DOCUMENTS

DE   1 99 24 311   11/2000

(Continued)

OTHER PUBLICATIONS

International Search Report from application EP 06004598 dated Jun. 22, 2006.

(Continued)

*Primary Examiner* — Scott A. Smith

(57) ABSTRACT

A surgical stapling apparatus including a cartridge assembly defining a first tissue contacting surface, an anvil assembly defining a second tissue contacting surface, and a surgical buttress releasably secured to at least one of the first tissue contacting surface and the second tissue contacting surface is provided. The buttress provides a uniform profile to be used on both the anvil and cartridge of a loading unit.

27 Claims, 10 Drawing Sheets

U.S. PATENT DOCUMENTS

| | | | |
|---|---|---|---|
| 5,575,803 A | 11/1996 | Cooper et al. | |
| 5,653,756 A | 8/1997 | Clarke et al. | |
| 5,683,809 A | 11/1997 | Freeman et al. | |
| 5,690,675 A | 11/1997 | Sawyer et al. | |
| 5,702,409 A | 12/1997 | Rayburn et al. | |
| 5,752,965 A | 5/1998 | Francis et al. | |
| 5,762,256 A | 6/1998 | Mastri et al. | |
| 5,766,188 A | 6/1998 | Igaki | |
| 5,769,892 A | 6/1998 | Kingwell | |
| 5,782,396 A | 7/1998 | Mastri et al. | |
| 5,799,857 A | 9/1998 | Robertson et al. | |
| 5,810,855 A | 9/1998 | Rayburn et al. | |
| 5,814,057 A | 9/1998 | Oi et al. | |
| 5,833,695 A | 11/1998 | Yoon | |
| 5,843,096 A | 12/1998 | Igaki et al. | |
| 5,895,412 A | 4/1999 | Tucker | |
| 5,902,312 A | 5/1999 | Frater et al. | |
| 5,908,427 A | 6/1999 | McKean et al. | |
| 5,915,616 A | 6/1999 | Viola et al. | |
| 5,931,847 A | 8/1999 | Bittner et al. | |
| 5,964,774 A | 10/1999 | McKean et al. | |
| 5,997,895 A | 12/1999 | Narotam et al. | |
| 6,019,791 A | 2/2000 | Wood | |
| 6,030,392 A | 2/2000 | Dakov | |
| 6,032,849 A | 3/2000 | Mastri et al. | |
| 6,045,560 A | 4/2000 | McKean et al. | |
| 6,063,097 A | 5/2000 | Oi et al. | |
| 6,080,169 A | 6/2000 | Turtel | |
| 6,099,551 A | 8/2000 | Gabbay | |
| 6,149,667 A | 11/2000 | Hovland et al. | |
| 6,155,265 A | 12/2000 | Hammerslag | |
| 6,210,439 B1 | 4/2001 | Firmin et al. | |
| 6,214,020 B1 | 4/2001 | Mulhauser et al. | |
| 6,241,139 B1 | 6/2001 | Milliman et al. | |
| 6,258,107 B1 | 7/2001 | Balazs et al. | |
| 6,267,772 B1 | 7/2001 | Mulhauser et al. | |
| 6,273,897 B1 | 8/2001 | Dalessandro et al. | |
| 6,280,453 B1 | 8/2001 | Kugel et al. | |
| 6,299,631 B1 | 10/2001 | Shalaby | |
| 6,312,457 B1 | 11/2001 | DiMatteo et al. | |
| 6,312,474 B1 | 11/2001 | Francis et al. | |
| 6,325,810 B1 | 12/2001 | Hamilton et al. | |
| 6,436,030 B2 | 8/2002 | Rehil | |
| 6,454,780 B1 | 9/2002 | Wallace | |
| 6,461,368 B2 | 10/2002 | Fogarty et al. | |
| 6,503,257 B2 | 1/2003 | Grant et al. | |
| 6,514,283 B2 | 2/2003 | DiMatteo et al. | |
| 6,517,566 B1 | 2/2003 | Hovland et al. | |
| 6,551,356 B2 | 4/2003 | Rousseau | |
| 6,592,597 B2 | 7/2003 | Grant et al. | |
| 6,638,285 B2 | 10/2003 | Gabbay | |
| 6,652,594 B2 | 11/2003 | Francis et al. | |
| 6,656,193 B2 | 12/2003 | Grant et al. | |
| 6,669,735 B1 | 12/2003 | Pelissier | |
| 6,677,258 B2 | 1/2004 | Carroll et al. | |
| 6,685,714 B2 | 2/2004 | Rousseau | |
| 6,704,210 B1 | 3/2004 | Myers | |
| 6,723,114 B2 | 4/2004 | Shalaby | |
| 6,726,706 B2 | 4/2004 | Dominguez | |
| 6,736,823 B2 | 5/2004 | Darois et al. | |
| 6,736,854 B2 | 5/2004 | Vadurro et al. | |
| 6,746,458 B1 | 6/2004 | Cloud | |
| 6,773,458 B1 | 8/2004 | Brauker et al. | |
| 6,927,315 B1 | 8/2005 | Heinecke et al. | |
| 7,128,748 B2 | 10/2006 | Mooradian et al. | |
| 7,147,138 B2 | 12/2006 | Shelton, IV | |
| 7,434,717 B2 | 10/2008 | Shelton, IV et al. | |
| 7,438,209 B1 | 10/2008 | Hess et al. | |
| 7,547,312 B2 | 6/2009 | Bauman et al. | |
| 7,559,937 B2 | 7/2009 | de la Torre et al. | |
| 7,604,151 B2 | 10/2009 | Hess et al. | |
| 7,665,646 B2 | 2/2010 | Prommersberger | |
| 7,744,627 B2 | 6/2010 | Orban, III et al. | |
| 7,793,813 B2 | 9/2010 | Bettuchi | |
| 7,823,592 B2 * | 11/2010 | Bettuchi et al. | 128/898 |
| 7,845,533 B2 | 12/2010 | Marczyk et al. | |
| 7,845,536 B2 | 12/2010 | Viola et al. | |
| 7,909,224 B2 * | 3/2011 | Prommersberger | 227/176.1 |
| 2002/0016626 A1 | 2/2002 | DiMatteo et al. | |
| 2002/0019187 A1 | 2/2002 | Carroll et al. | |
| 2002/0052622 A1 | 5/2002 | Rousseau | |
| 2002/0091397 A1 | 7/2002 | Chen | |
| 2002/0133236 A1 | 9/2002 | Rousseau | |
| 2002/0138152 A1 | 9/2002 | Francis et al. | |
| 2002/0151911 A1 | 10/2002 | Gabbay | |
| 2002/0165559 A1 | 11/2002 | Grant et al. | |
| 2002/0165562 A1 | 11/2002 | Grant et al. | |
| 2002/0165563 A1 | 11/2002 | Grant et al. | |
| 2002/0177859 A1 | 11/2002 | Monassevitch et al. | |
| 2003/0065345 A1 | 4/2003 | Weadock | |
| 2003/0065346 A1 | 4/2003 | Evens et al. | |
| 2003/0083676 A1 | 5/2003 | Wallace | |
| 2003/0088256 A1 | 5/2003 | Conston et al. | |
| 2003/0105510 A1 | 6/2003 | DiMatteo et al. | |
| 2003/0114866 A1 | 6/2003 | Ulmsten et al. | |
| 2003/0120284 A1 | 6/2003 | Palacios et al. | |
| 2003/0167064 A1 | 9/2003 | Whayne | |
| 2003/0181927 A1 | 9/2003 | Wallace | |
| 2003/0183671 A1 | 10/2003 | Mooradian et al. | |
| 2003/0208231 A1 | 11/2003 | Williamson, IV et al. | |
| 2004/0034377 A1 | 2/2004 | Sharkawy et al. | |
| 2004/0092960 A1 | 5/2004 | Abrams et al. | |
| 2004/0093029 A1 | 5/2004 | Zubik et al. | |
| 2004/0107006 A1 | 6/2004 | Francis et al. | |
| 2004/0116945 A1 | 6/2004 | Sharkawy et al. | |
| 2004/0142621 A1 | 7/2004 | Carroll et al. | |
| 2004/0172048 A1 | 9/2004 | Browning | |
| 2004/0209059 A1 | 10/2004 | Foss | |
| 2004/0215214 A1 | 10/2004 | Crews et al. | |
| 2004/0215219 A1 | 10/2004 | Eldridge et al. | |
| 2004/0215221 A1 | 10/2004 | Suyker et al. | |
| 2004/0254590 A1 | 12/2004 | Hoffman et al. | |
| 2004/0260315 A1 | 12/2004 | Dell et al. | |
| 2005/0002981 A1 | 1/2005 | Lahtinen et al. | |
| 2005/0021026 A1 | 1/2005 | Baily | |
| 2005/0021053 A1 | 1/2005 | Heinrich | |
| 2005/0021085 A1 | 1/2005 | Abrams et al. | |
| 2005/0059996 A1 | 3/2005 | Bauman et al. | |
| 2005/0059997 A1 | 3/2005 | Bauman et al. | |
| 2005/0070929 A1 | 3/2005 | Dalessandro et al. | |
| 2005/0118435 A1 | 6/2005 | DeLucia et al. | |
| 2005/0228446 A1 | 10/2005 | Mooradian et al. | |
| 2005/0245965 A1 | 11/2005 | Orban et al. | |
| 2006/0004407 A1 | 1/2006 | Hiles et al. | |
| 2006/0085034 A1 | 4/2006 | Bettuchi | |
| 2006/0135992 A1 | 6/2006 | Bettuchi et al. | |
| 2006/0173470 A1 | 8/2006 | Oray et al. | |
| 2006/0178683 A1 | 8/2006 | Shimoji et al. | |
| 2006/0212050 A1 | 9/2006 | D'Agostino et al. | |
| 2006/0271104 A1 | 11/2006 | Viola et al. | |
| 2007/0034669 A1 | 2/2007 | de la Torre et al. | |
| 2007/0049953 A2 | 3/2007 | Shimoji et al. | |
| 2007/0179528 A1 | 8/2007 | Soltz et al. | |
| 2007/0203509 A1 | 8/2007 | Bettuchi | |
| 2007/0203510 A1 | 8/2007 | Bettuchi | |
| 2007/0246505 A1 | 10/2007 | Pace-Floridia et al. | |
| 2008/0029570 A1 | 2/2008 | Shelton et al. | |
| 2008/0082126 A1 | 4/2008 | Murray et al. | |
| 2008/0110959 A1 | 5/2008 | Orban et al. | |
| 2008/0125812 A1 | 5/2008 | Zubik et al. | |
| 2008/0140115 A1 | 6/2008 | Stopek | |
| 2008/0161831 A1 | 7/2008 | Bauman et al. | |
| 2008/0161832 A1 | 7/2008 | Bauman et al. | |
| 2008/0169327 A1 | 7/2008 | Shelton et al. | |
| 2008/0169328 A1 | 7/2008 | Shelton | |
| 2008/0169329 A1 | 7/2008 | Shelton et al. | |
| 2008/0169330 A1 | 7/2008 | Shelton et al. | |
| 2008/0169331 A1 | 7/2008 | Shelton et al. | |
| 2008/0169332 A1 | 7/2008 | Shelton et al. | |
| 2008/0169333 A1 | 7/2008 | Shelton et al. | |
| 2008/0290134 A1 | 11/2008 | Bettuchi et al. | |
| 2008/0308608 A1 | 12/2008 | Prommersberger | |
| 2008/0314960 A1 | 12/2008 | Marczyk et al. | |
| 2009/0001121 A1 | 1/2009 | Hess et al. | |
| 2009/0001122 A1 | 1/2009 | Prommersberger et al. | |
| 2009/0001123 A1 | 1/2009 | Morgan et al. | |
| 2009/0001124 A1 | 1/2009 | Hess et al. | |

| | | | |
|---|---|---|---|
| 2009/0001125 A1 | 1/2009 | Hess et al. | |
| 2009/0001126 A1 | 1/2009 | Hess et al. | |
| 2009/0001128 A1 | 1/2009 | Weisenburgh, II et al. | |
| 2009/0001130 A1 | 1/2009 | Hess et al. | |
| 2009/0005808 A1 | 1/2009 | Hess et al. | |
| 2009/0030452 A1 | 1/2009 | Bauman et al. | |
| 2009/0043334 A1 | 2/2009 | Bauman et al. | |
| 2009/0078739 A1 | 3/2009 | Viola | |
| 2009/0095791 A1 | 4/2009 | Eskaros et al. | |
| 2009/0095792 A1 | 4/2009 | Bettuchi | |
| 2009/0120994 A1 | 5/2009 | Murray et al. | |
| 2009/0134200 A1 | 5/2009 | Tarinelli et al. | |
| 2009/0206125 A1 | 8/2009 | Huitema et al. | |
| 2009/0206126 A1 | 8/2009 | Huitema et al. | |
| 2009/0206139 A1 | 8/2009 | Hall et al. | |
| 2009/0206141 A1 | 8/2009 | Huitema et al. | |
| 2009/0206142 A1 | 8/2009 | Huitema et al. | |
| 2009/0206143 A1 | 8/2009 | Huitema et al. | |
| 2009/0218384 A1 | 9/2009 | Aranyi | |
| 2009/0277947 A1 | 11/2009 | Viola | |
| 2009/0287230 A1 | 11/2009 | D'Agostino et al. | |
| 2010/0012704 A1 | 1/2010 | Tarinelli Racenet et al. | |
| 2010/0065606 A1 | 3/2010 | Stopek | |
| 2010/0065607 A1 | 3/2010 | Orban, III et al. | |
| 2010/0072254 A1 | 3/2010 | Aranyi et al. | |
| 2010/0147921 A1 | 6/2010 | Olson | |
| 2010/0147922 A1 | 6/2010 | Olson | |
| 2010/0147923 A1 | 6/2010 | D'Agostino et al. | |
| 2010/0243707 A1 | 9/2010 | Olson et al. | |
| 2010/0243708 A1 | 9/2010 | Aranyi et al. | |
| 2010/0243711 A1 | 9/2010 | Olson et al. | |
| 2010/0249805 A1 | 9/2010 | Olson et al. | |
| 2010/0264195 A1 | 10/2010 | Bettuchi | |
| 2010/0282815 A1 | 11/2010 | Bettuchi et al. | |
| 2011/0024476 A1 | 2/2011 | Bettuchi et al. | |
| 2011/0024481 A1 | 2/2011 | Bettuchi et al. | |
| 2011/0036894 A1 | 2/2011 | Bettuchi | |
| 2011/0042442 A1 | 2/2011 | Viola et al. | |
| 2011/0046650 A1 | 2/2011 | Bettuchi | |
| 2011/0057016 A1 | 3/2011 | Bettuchi | |

FOREIGN PATENT DOCUMENTS

| | | |
|---|---|---|
| DE | 199 24 311 A1 | 11/2000 |
| EP | 0 594 148 | 4/1994 |
| EP | 0 594 148 A1 | 4/1994 |
| EP | 0 327 022 | 4/1995 |
| EP | 0 327 022 B1 | 4/1995 |
| EP | 0 667 119 A1 | 8/1995 |
| EP | 1 064 883 A1 | 1/2001 |
| EP | 1 256 317 A2 | 11/2002 |
| EP | 1 520 525 | 4/2005 |
| EP | 1 520 525 A1 | 4/2005 |
| EP | 1 621 141 | 2/2006 |
| EP | 1 759 640 A2 | 3/2007 |
| EP | 2 005 894 A2 | 12/2008 |
| EP | 2 005 895 A2 | 12/2008 |
| WO | WO 90/05489 | 5/1990 |
| WO | WO 90/05489 A1 | 5/1990 |
| WO | WO 97/01989 A1 | 1/1997 |
| WO | WO 98/17180 | 4/1998 |
| WO | WO 98/17180 A1 | 4/1998 |
| WO | WO 99/45849 | 9/1999 |
| WO | WO 99/45849 A1 | 9/1999 |
| WO | WO 03/082126 A1 | 10/2003 |
| WO | WO 03/105698 A2 | 12/2003 |
| WO | WO 2006/023578 | 3/2006 |
| WO | WO 2006/023578 A2 | 3/2006 |
| WO | WO 2006/044490 | 4/2006 |
| WO | WO 2006/044490 A2 | 4/2006 |
| WO | WO 2006/083748 A1 | 8/2006 |
| WO | WO 2008/057281 A2 | 5/2008 |
| WO | WO 2008/109125 A1 | 9/2008 |

OTHER PUBLICATIONS

International Search Report from application EP 06016962.0 dated Jan. 3, 2007.
International Search Report from Application No. PCT/US05/36740 mailed Mar. 23, 2007.
International Search Report from Application No. PCT/US2008/002981 dated Jun. 26, 2008.
International Search Report from Application No. EP 08 25 1779 dated Jul. 23, 2008.
International Search Report corresponding to European Application No. EP 10 25 0715.9, completed on Jun. 30, 2010 and mailed on Jul. 20, 2010; 3 pages.
International Search Report corresponding to European Application No. EP 10 25 0642.5, completed on Mar. 25, 2011 and mailed on Apr. 4, 2011; 4 pages.
International Search Report corresponding to European Application No. EP 06 00 4598, completed on Jun. 22, 2006; 2 pages.
International Search Report corresponding to European Application No. EP 06 01 6962.0, completed on Jan. 3, 2007 and mailed on Jan. 11, 2007; 10 pages.
International Search Report corresponding to International Application No. PCT/US05/36740, completed on Feb. 20, 2007 and mailed on Mar. 23, 2007; 8 pages.
International Search Report corresponding to International Application No. PCT/US2008/002981, completed on Jun. 9, 2008 and mailed on Jun. 26, 2008; 2 pages.
International Search Report corresponding to European Application No. EP 08 25 1779, completed on Jul. 14, 2008 and mailed on Jul. 23, 2008; 5 pages.
International Search Report corresponding to European Application No. EP 08 25 1989.3, completed on Mar. 11, 2010 and mailed on Mar. 24, 2010; 3 pages.
International Search Report corresponding to European Application No. EP 10 25 1437.9, completed on Nov. 22, 2010 and mailed on Dec. 16, 2010; 3 pages.
International Search Report corresponding to European Application No. EP 09 25 2897.5, completed on Feb. 7, 2011 and mailed on Feb. 15, 2011; 3 pages.

* cited by examiner

STAPLE LINE REINFORCEMENT FOR ANVIL AND CARTRIDGE

BACKGROUND

1. Technical Field

The present disclosure relates to a surgical stapling apparatus and, more particularly, to a surgical stapling apparatus including a detachable surgical buttress for an anvil and a staple cartridge.

2. Background of Related Art

Surgical stapling instruments that are used to sequentially or simultaneously apply one or more rows of fasteners to join segments of body tissues are well known in the art. The fasteners are typically in the form of surgical staples but two part polymeric fasteners can also be utilized. Such devices generally include a pair of jaws to clamp therebetween the body tissues to be joined. Typically, one of the jaw members includes a staple cartridge which accommodates a plurality of staples arranged in at least two lateral rows while the other jaw member has an anvil that defines a surface for forming the staple legs as the staples are driven from the staple cartridge.

When the stapling instrument is actuated, longitudinally translating cams contact staple drive members in one of the jaws which in turn acts upon staple pushers to sequentially or simultaneously eject the staples from the staple cartridge. A blade can travel between the staple rows to longitudinally cut and/or open the stapled tissue between the rows of staples. Such instruments are disclosed, for example, in U.S. Pat. No. 3,079,606 and U.S. Pat. No. 3,490,675.

When stapling relatively thin or fragile tissues, it is important to effectively seal the staple line against air or fluid leakage. Additionally, it is often necessary to reinforce the staple line against the tissue to prevent tears in the tissue or pulling of the staples through the tissue. One method of preventing tears or pull through involves the placement of a biocompatible fabric reinforcing material, or a "buttress," between the staple and the underlying tissue. In this method, a layer of buttress material is placed against the tissue and the tissue is stapled in conventional manner. In more recent methods, the layer of buttress is positioned on the stapling instrument itself prior to stapling the tissue. Some surgical staplers utilize fasteners or clips to temporarily connect buttress material to each of the jaws of the staplers, i.e., one disposed on the staple cartridge assembly and the other on the anvil assembly.

It is a desire of the present application to provide a staple line reinforcement profile which simultaneously incorporates features which satisfy the requirements of one or more different assemblies. It would also be desirable to provide a single profile buttress that can be used on a surgical staple cartridge assembly and/or a surgical anvil cartridge assembly. Accordingly, it is an object of this disclosure to meet the aforementioned desires.

SUMMARY

The present disclosure relates to a surgical stapling apparatus including a surgical buttress.

According to an aspect of the present disclosure, a surgical stapling apparatus is provided and includes a cartridge assembly defining a first tissue contacting surface, the cartridge assembly housing a plurality of surgical fasteners therein, the cartridge assembly defining at least one distal attachment point and at least one proximal attachment point; an anvil assembly defining a second tissue contacting surface, the anvil assembly movably secured in relation to cartridge assembly, the anvil assembly defining at least one distal attachment point and at least one proximal attachment point, wherein the at least one proximal attachment point of the anvil assembly is offset an axial distance from the at least one proximal attachment point of the cartridge assembly; and a surgical buttress releasably secured to each of the first tissue contacting surface and the second tissue contacting surface, the surgical buttress including a body portion configured to substantially overlie at least one of the first and second tissue contacting surfaces of either the first length and second length cartridge assembly and anvil assembly.

Each surgical buttress defines a distal attachment feature for registration with the distal attachment point of the cartridge assembly and the anvil assembly; and a first proximal attachment feature and a second proximal attachment feature offset an axial distance from the first proximal attachment feature. The first proximal attachment feature registers with the proximal attachment point of the cartridge assembly; and the second proximal attachment feature registers with the proximal attachment point of the anvil assembly.

The surgical buttress may be disposed against the tissue contact surface of the cartridge assembly and the surgical buttress may be disposed against the tissue contact surface of the anvil assembly have substantially the same length.

Each surgical buttress may have the same configuration. Each surgical buttress may be fabricated from a biocompatible and bioabsorbable material.

The surgical stapling apparatus may further include sutures retaining surgical buttresses against the tissue contacting surface of the cartridge assembly and the anvil assembly.

The surgical stapling apparatus may further include a suture retaining a distal end portion of the surgical buttress against a respective one of the cartridge assembly and the anvil assembly, wherein the suture maintains the distal attachment feature of the surgical buttress in registration with the distal attachment point of the respective one of the cartridge assembly and the anvil assembly.

The surgical stapling apparatus may further include a suture retaining a proximal end portion of the surgical buttress against a respective one of the cartridge assembly and the anvil assembly, wherein a suture maintains the first proximal attachment feature of the surgical buttress in registration with the proximal attachment point of the cartridge assembly and the anvil assembly, and wherein a suture maintains the second proximal attachment feature of the surgical buttress in registration with the proximal attachment point of the anvil assembly.

According to another aspect of the present disclosure, a surgical stapling apparatus is provided and includes a cartridge assembly defining a first tissue contacting surface, the cartridge assembly housing a plurality of surgical fasteners therein, the cartridge assembly being either a first length or a second length longer than the first length; an anvil assembly defining a second tissue contacting surface, the anvil assembly movably secured in relation to cartridge assembly, the anvil assembly being either the first length or the second length each corresponding to the length of the cartridge assembly; and a surgical buttress releasably secured to at least one of the first tissue contacting surface and the second tissue contacting surface, the surgical buttress including a head portion, a neck portion, and a body portion. The head portion is connected to a distal end of the body portion by the neck portion. The surgical buttress is configured to substantially overlie at least one of the first and second tissue contacting surfaces of either the first length and second length cartridge assembly and anvil assembly.

The body portion of the surgical buttress may define a recess formed in a proximal edge thereof, the recess longitudinally bisecting the proximal edge. The recess may be a notch having a v-shape profile.

The body portion of the surgical buttress may define at least one pair of opposing proximal recesses, and each of the at least one pair of opposing proximal recesses may be formed on an opposing lateral side of the body portion near a proximal edge of the surgical buttress. The at least one pair of opposing proximal recesses may be a notch having a v-shape profile.

The body portion of the surgical buttress may further define a pair of opposing distal recesses, and each of the pair of opposing distal recesses may be formed on an opposing lateral side of the body portion near a distal edge of the body portion.

The pair of opposing distal recesses may be longitudinally tapered. A distal edge of the body portion of the surgical buttress may be arcuated. A distal edge of the body portion of the surgical buttress may have a transverse width dimension less than that of the rest of the body portion. The head portion may have a substantially rectangular shape.

Each surgical buttress may be fabricated from a biocompatible and bioabsorbable material.

According to a further aspect of the present disclosure, a surgical buttress for use in a surgical stapling apparatus is provided. The surgical buttress includes a body portion; a neck portion; and a head portion connected to a distal end of the body portion by the neck portion, wherein the body portion defines at least one pair of opposing proximal recesses, each of the at least one pair of opposing proximal recesses is formed on an opposing lateral side of the body portion near a proximal edge of the body portion.

Each of the at least one pair of opposing proximal recesses may be a notch having a v-shape profile. The body portion may further define a pair of opposing distal recesses, each of the pair of opposing distal recesses may be formed on an opposing lateral side of the body portion near a distal edge of the body portion.

The body portion of the surgical buttress may further define a proximal edge recess formed in a proximal edge thereof, the proximal edge recess longitudinally bisecting the proximal edge. A distal edge of the body portion of the surgical buttress may be arcuated. A distal edge of the body portion of the surgical buttress may have a transverse width dimension less than that of the rest of the body portion. The head portion may have a substantially rectangular shape.

The surgical buttress may be fabricated from a biocompatible and bioabsorbable material.

According to still another aspect of the present disclosure, a surgical buttress is provided for use with a surgical stapling apparatus having a cartridge assembly of any number of lengths and an anvil assembly of any number of lengths corresponding to the lengths of the cartridge assembly, wherein each of the cartridge assembly and anvil assembly defines respective juxtaposed tissue contacting surfaces, and wherein the cartridge assembly includes a plurality of staples stored in staple slots thereof for formation against staple formation pockets of the anvil assembly. The surgical buttress includes a body portion configured and dimensioned to overlie all of the staple slots of the cartridge assembly for any length cartridge assembly, and/or overlie all of the staple formation pockets of the anvil assembly for any length anvil assembly. The surgical buttress further includes a neck portion extending from the body portion; and a head portion connected to the neck portion and opposite a distal end of the body portion, wherein the body portion defines at least one pair of opposing proximal recesses, each of the at least one pair of opposing proximal recesses is formed on an opposing lateral side of the body portion near a proximal edge of the body portion.

BRIEF DESCRIPTION OF THE DRAWINGS

The present disclosure will be further described with reference to the accompanying drawings, wherein like reference numerals refer to like parts in the several views, and wherein.

DETAILED DESCRIPTION OF EMBODIMENTS

Figure 1:
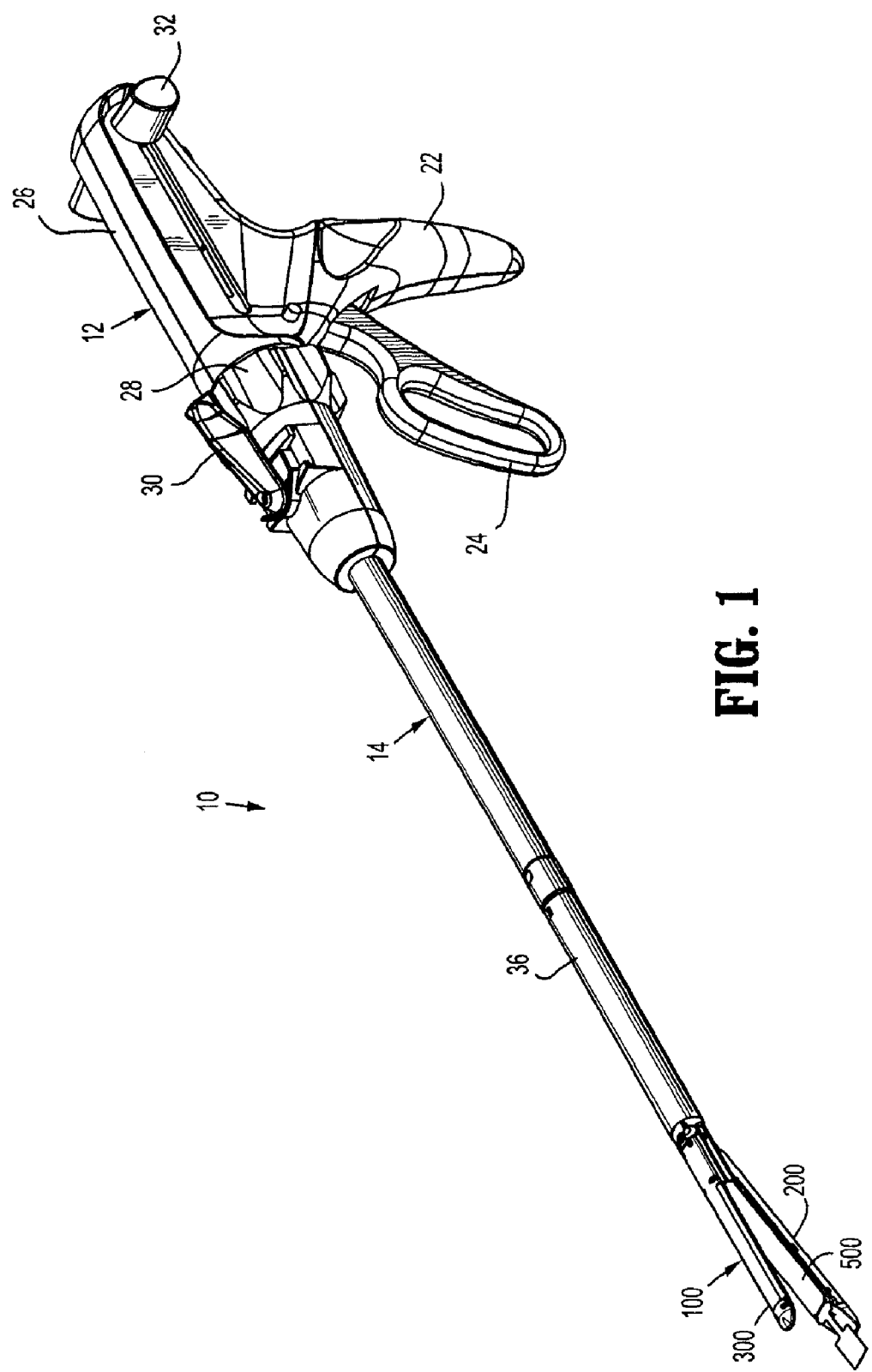
FIG. 1 is a perspective view of a surgical stapling apparatus according to an embodiment of the present disclosure.

Embodiments of the presently disclosed staple line reinforcement for anvil and cartridge of a loading unit of a surgical stapling apparatus will now be described in detail with reference to the drawings, in which like reference numerals designate identical or corresponding elements in each of the several views. In the drawings and in the description that follows, the term "proximal," as is traditional, will refer to the end of the stapling apparatus which is closest to the operator, while the term "distal" will refer to the end of the apparatus which is farthest from the operator.

Referring now to FIG. 1, there is disclosed a linear surgical stapling apparatus, generally referred to as 10. In the interest of brevity, this disclosure will focus primarily on a buttress utilized in a loading unit 100, e.g., a single use loading unit ("SULU") or a disposable loading unit ("DLU"). For simplicity, hereinafter, SULU or DLU will be referred to as "DLU," but it should be understood to include either or both a DLU or SULU. An exemplary example of this type of surgical stapling instrument is disclosed in U.S. Pat. No. 7,128,253, the entire disclosure of which is incorporated by reference herein.

Surgical stapling apparatus 10 generally includes a handle assembly 12 and an elongate body 14 extending distally from handle assembly 12. A DLU 100 is releasably secured to the distal end of elongate body 14. DLU 100 includes a cartridge assembly 200 housing a plurality of surgical fasteners or staples 223 (see FIG. 2) and an anvil assembly 300 movably secured in relation to cartridge assembly 200. Handle assembly 12 includes a stationary handle member 22, a movable handle member 24, and a barrel portion 26. An articulation lever 30 is mounted on the forward end of barrel portion 26 adjacent rotatable member 28 to facilitate articulation of DLU 100. A pair of knobs 32 are movably positioned along barrel portion 26. Knobs 32 are advanced distally to approximate or close cartridge and/or anvil assembly 200, 300, and retracted proximally to unapproximate or open cartridge and/or anvil assembly 200, 300. Actuation of movable handle member 24 applies lines of staples 223 to tissue. In order to properly orient cartridge and anvil assembly 200, 300 relative to the tissue to be stapled, surgical stapling apparatus 10 is additionally provided with a rotatable member 28 on the forward end of barrel portion 26. Rotation of rotatable member 28 relative to handle assembly 12 rotates elongate body 14 and loading unit 100 relative to handle assembly 12 so as to properly orient cartridge assembly 200 and anvil assembly 300 relative to the tissue to be stapled.

Figure 2:
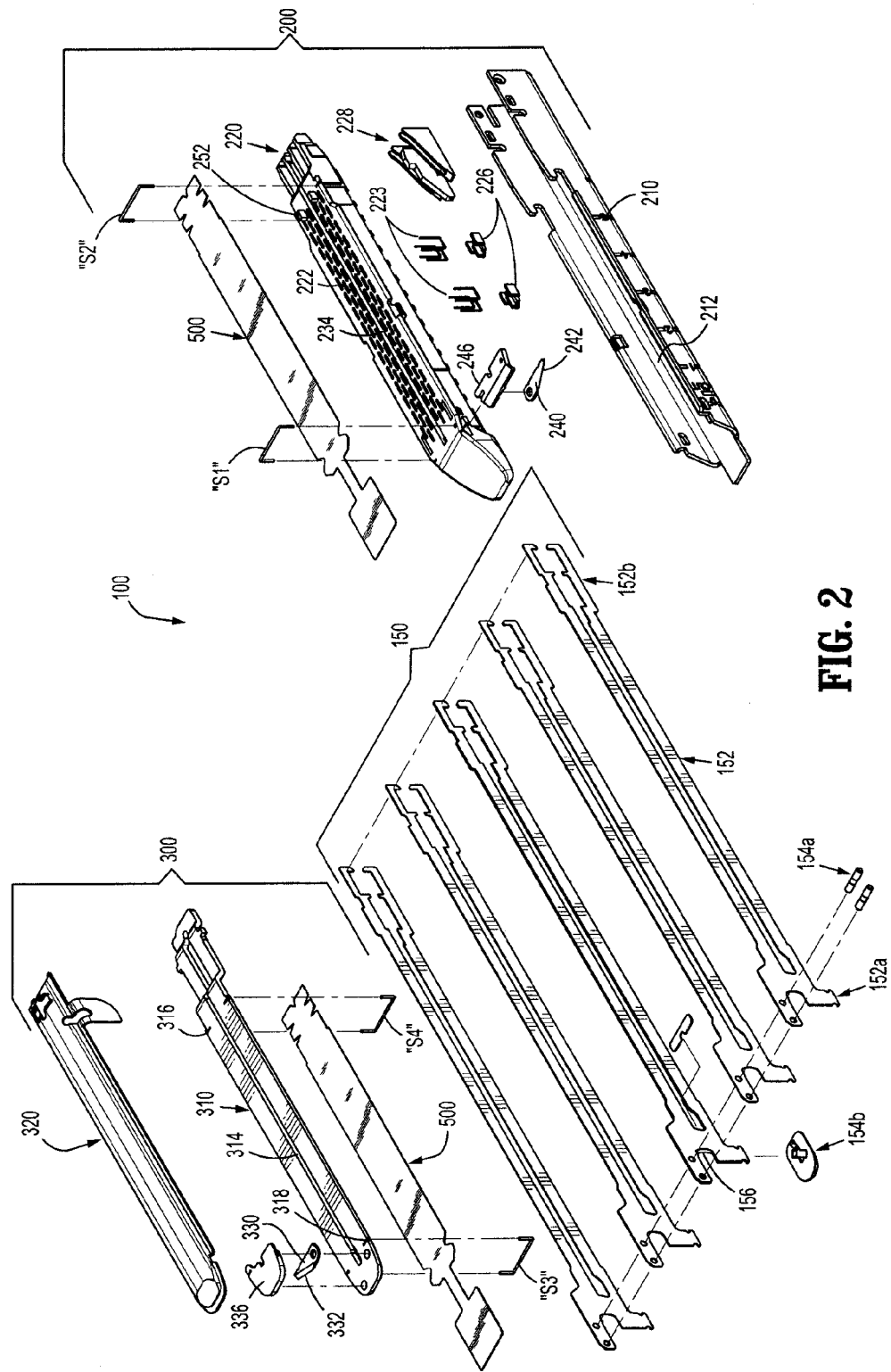
FIG. 2 is a top, exploded, perspective view of a distal end of a DLU of the surgical stapling apparatus of FIG. 1.

As seen in FIG. 2, cartridge assembly 200 includes a carrier 210 defining an elongated support channel 212. Elongated support channel 212 of carrier 210 is dimensioned and configured to selectively receive a staple cartridge 220 therein. Staple cartridge 220 includes retention slots 222 formed therein for receiving a plurality of fasteners 223 and pushers 226. A plurality of spaced apart longitudinal slots extend through staple cartridge 220 to accommodate upstanding cam wedges of actuation sled 228. A central longitudinal slot 234 is formed in and extends along the length of staple cartridge 220 to facilitate passage of knife blade 156 of drive bar 150 therethrough. During operation of surgical stapler 10, actuation sled 228 translates through staple cartridge 220 to advance the cam wedges into sequential contact with pushers 226, to cause pushers 226 to translate vertically within retention slots 222 and urge staples 223 from slots 222 into staple forming cavities of anvil plate 310 of anvil assembly 300.

Figure 10:
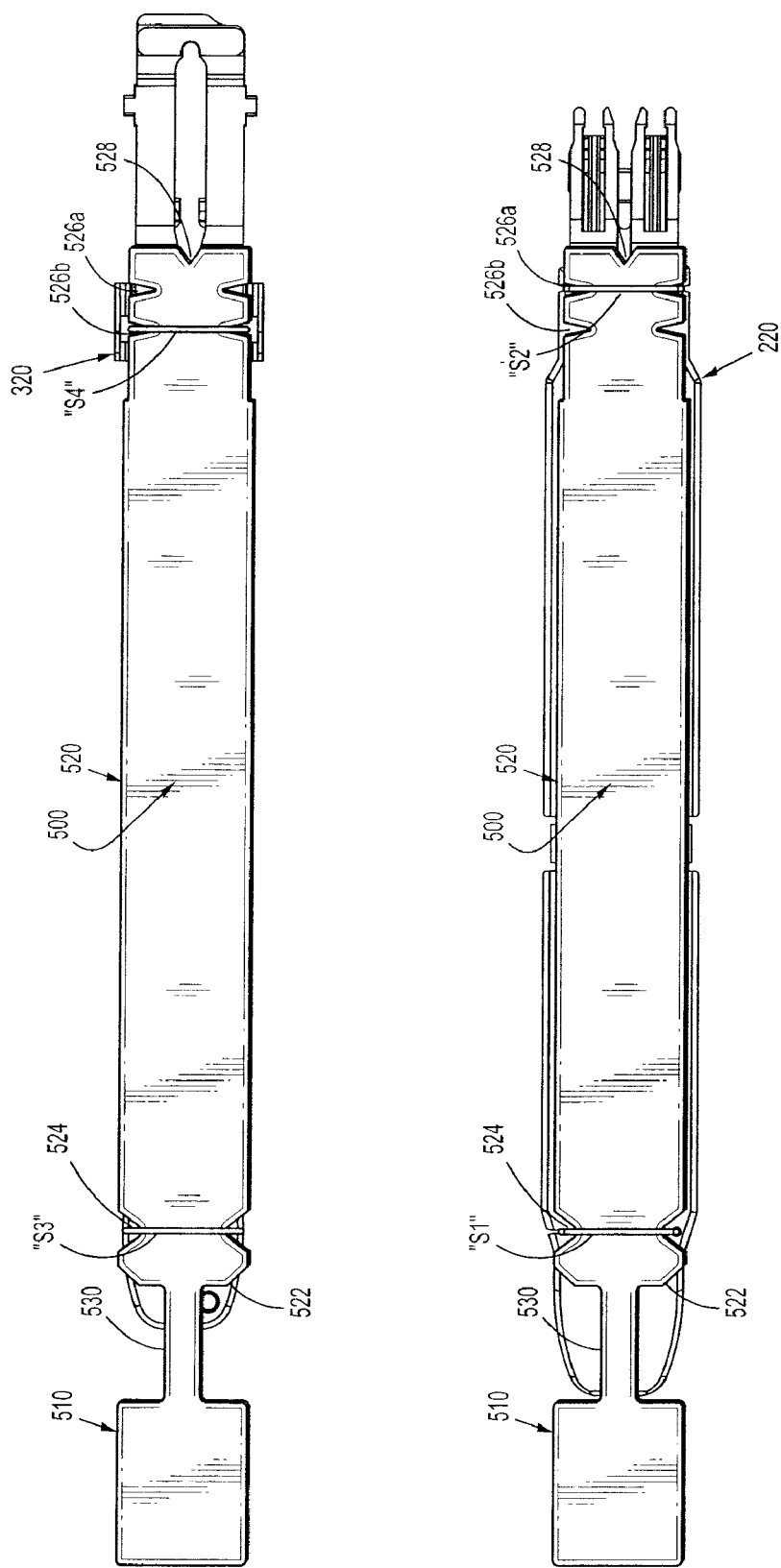
FIG. 10 is a plan view of the cartridge assembly of the DLU of FIGS. 4-8 and the anvil assembly of the DLU of FIG. 9, illustrating the attachment of the buttress of FIG. 3 at different attachment points of a respective cartridge assembly and anvil assembly.

As seen in FIG. 2, cartridge assembly 200 includes a surgical cartridge buttress 500 operatively secured to an upper surface of staple cartridge 220, by sutures "S1, S2," to overlie at least some of retention slots 222 and/or at least a portion of a length of longitudinal slot 234. A first suture "S1" is threaded through each of a distal pair of recesses or attachment points 238 and around/over distal portion of cartridge buttress 500 and, and a second suture "S2" is threaded through each of a proximal pair of recesses or attachment points 236 and around/over proximal portion of cartridge buttress 500. A first end of each suture "S1, S2" may be anchored or fixed in a respective one recesses of the proximal and distal pair of recesses or attachment points 236, 238 while a second end of each suture "S1, S2" passes transversely across respective distal and proximal portions of cartridge buttress 500 and is anchored or fixed in a respective other recess of the proximal and distal pair of recesses or attachment points 236, 238. As seen in FIG. 10, cartridge assembly 200 defines an axial distance "D1" between the distal pair of recesses or attachment points 238 and the proximal pair of recesses or attachment points 236.

Figure 9:
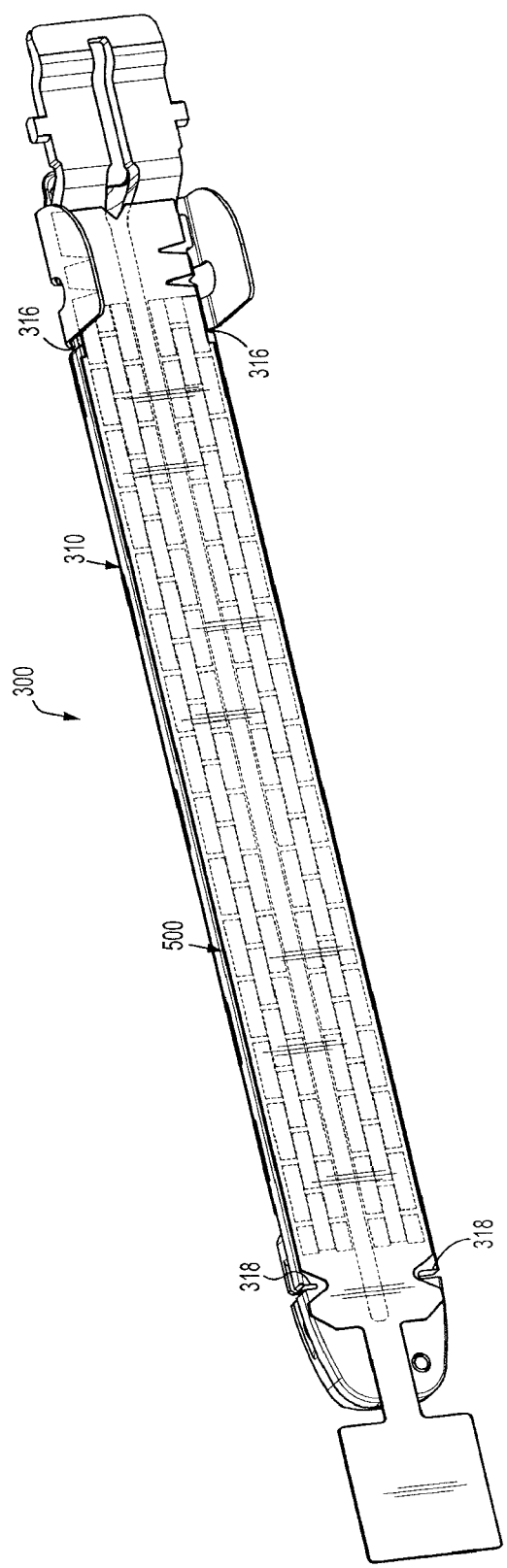
FIG. 9 is a perspective view of an anvil assembly of the DLU of FIG. 2, illustrating the buttress of FIG. 3 secured thereto.

With reference still to FIG. 2, anvil assembly 300 includes an anvil plate 310 having a plurality of staple deforming pockets/cavities 310a (see FIG. 9) and a cover plate 320 secured to a top surface of anvil plate 310. Anvil assembly 300 further includes a knife blade 330 operatively interposed within the cavity defined between anvil plate 310 and cover plate 320.

Anvil plate 310 defines a proximal pair of recesses or attachment points 316 formed near a proximal end of anvil plate 310 and disposed, one each, on opposed sides of longitudinal slot 314. Anvil plate 310 defines a distal pair of recesses or attachment points 318 formed near a distal end of anvil plate 310 and disposed, one each, on opposed sides of longitudinal slot 314. At least one recess of each of the proximal pair of recesses or attachment points 316 and the distal pair of recesses or attachment points 318 is in the form of a slot or notch having a constricting profile so as to frictionally engage and/or pinch a suture "S". Anvil assembly 300 further includes a surgical anvil buttress 500 operatively secured to a lower surface of anvil plate 310, by sutures "S3, S4," to overlie at least some of anvil pockets 310a and/or at least a portion of a length of longitudinal slot 314.

With reference still to FIG. 2, anvil buttress 500 is secured to a lower surface of anvil plate 310, by anchors "S3, S4", to overlie at least some of the anvil pockets and/or at least a portion of a length of longitudinal slot 314. In particular, an anchor "S3" is threaded across a distal portion of the anvil buttress 500 and each of the corresponding distal pair of recesses or attachment points 318, and an anchor "S4" is threaded across a proximal portion of anvil buttress 500 and each of the corresponding proximal pair of recesses or attachment points 316. As seen in FIG. 10, anvil assembly 300 defines an axial distance "D2" between the distal pair of recesses or attachment points 318 and the proximal pair of recesses or attachment points 316.

Reference may be made to U.S. patent application Ser. No. 12/342,400, filed on Dec. 23, 2008, the entire content of which is incorporated herein by reference, for a detailed discussion of the construction and operation of surgical stapling apparatus 10, cartridge assembly 200 and/or anvil assembly 300.

Buttress 500 for each of cartridge assembly 200 and anvil assembly 300 is provided to reinforce and seal staple lines applied to tissue by surgical stapling apparatus 10. Cartridge assembly 200 and anvil assembly 300 are particularly configured to allow surgical buttresses 500 to be localized on inwardly facing surfaces of cartridge assembly 200 and anvil assembly 300 in order to facilitate passage of surgical stapling apparatus 10 into the body of a patient without risk of tearing or wrinkling of the respective buttresses as surgical stapling apparatus 10 is inserted into and manipulated within the body of a patient. The material from which the buttress 500 is formed may be bioabsorbable or non-bioabsorbable. It should be understood that any combination of natural, synthetic, bioabsorbable and non-bioabsorbable materials may be used to form the buttress material. The buttress material may be porous or non-porous, combination of porous and non-porous layers. The non-porous buttress material may be utilized to retard or prevent tissue ingrowth from surrounding tissues thereby acting as an adhesion barrier and preventing the formation of unwanted scar tissue.

Additional exemplary materials for surgical buttresses 500 for use with the surgical stapling devices disclosed herein are set forth in commonly assigned U.S. Pat. Nos. 5,542,594; 5,908,427; 5,964,774; and 6,045,560, and commonly assigned U.S. Application Publication Nos. 2006/0085034, filed on Apr. 20, 2006; and 2006/0135992, filed on Jun. 22, 2006, the entire contents of each of which is incorporated herein by reference.

In an embodiment, surgical buttresses 500 may be fabricated from a suitable biocompatible and bioabsorbable material. Surgical buttresses 500 may also be fabricated from a non-absorbent material which does not retain fluid, for example, surgical buttresses 500 may be fabricated from "BIOSYN™" (a synthetic polyester, commercially available from Tyco Healthcare Group, LP d/b/a COVIDIEN, North Haven, Conn.), which is made from "GLYCOMER 631" (a block copolymer) which is a synthetic polyester composed of glycolide, dioxanone and trimethylene carbonate.

One block of the resulting copolymer contains randomly combined units derived from p-dioxanone (1,4-dioxan-2-one) and trimethylene carbonate (1,3-dioxan-2-one). A second block of the copolymer contains randomly combined units derived from glycolide and p-dioxanone. The resulting polyester is an ABA triblock terpolymer possessing about 60% glycolide, about 14% dioxanone, and about 26% trimethylene carbonate.

Anvil buttress and/or cartridge buttress 500 may be pre-loaded (i.e., from the manufacturer) onto anvil assembly 300 or cartridge assembly 200. Additional or replacement buttresses 500 for anvil assembly 300 and/or cartridge assembly 200 may be secured to either anvil assembly 300 or cartridge assembly 200 as needed or desired.

In operation, with DLU 100 coupled to a distal end of elongated body 14 of surgical stapling apparatus 10, and with anvil and cartridge buttresses 500 pre-loaded onto anvil assembly 300 and cartridge assembly 200, respectively, surgical stapling apparatus 10 is used in accordance with methods known by those skilled in the art. Once anvil assembly 300 and cartridge assembly 200 are clamped onto tissue, surgical stapling apparatus 10 is fired. In firing surgical stapling apparatus 10, drive bar 150 is advanced from a proximal-most position to a distal-most position of DLU 100. In so doing, knife blade 156 of drive bar 150 enters notch 528 of buttress 500 thereby facilitating the dividing of buttress 500 and reducing any incidents of pushing or bunching-up of buttress 500 by blade 156. As drive bar 150 begins to travel distally, knife blade 156 substantially simultaneously cuts through a central section of the proximal anchors "S2, S4" of anvil assembly 300 and cartridge assembly 200, thereby respectively freeing the proximal ends of anvil and cartridge buttresses 500 therefrom. As knife blade 156 is moved distally, knife blade 156 slices or cuts longitudinally through both anvil buttress 500 and cartridge buttress 500, thereby dividing the buttresses 500 substantially in half.

Additionally, as drive bar 150 approaches the distal-most position, drive bar 150 and/or knife blade 156 engage a suture cutting assembly or suture release assembly, as described in U.S. patent application Ser. No. 12/342,400, filed on Dec. 23, 2008, the entire content of which is incorporated herein by reference, to thereby sever or release distal sutures "S1 or S3" and thus release a distal end of buttress 500.

Figure 3:
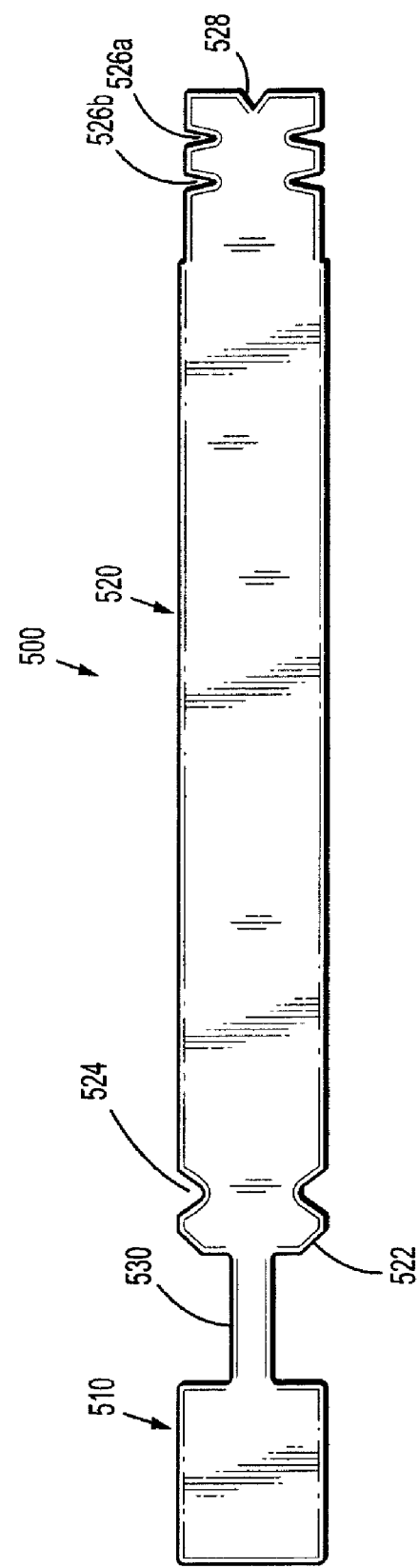
FIG. 3 is a top plan view of a buttress according to an embodiment of the present disclosure.
Figure 4:
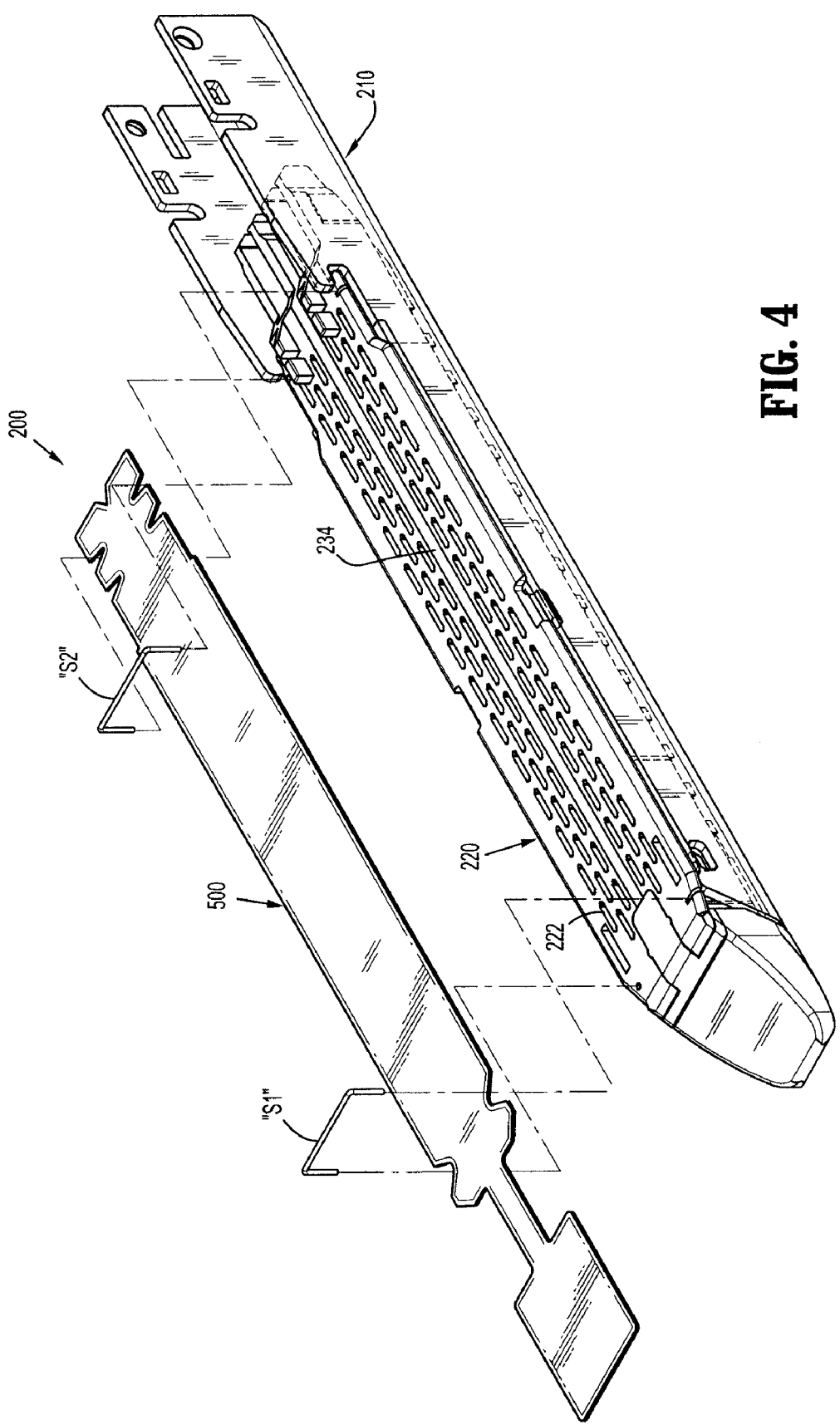
FIG. 4 is a top, perspective view of a cartridge half-section of the DLU of FIG. 2.
Figure 5:
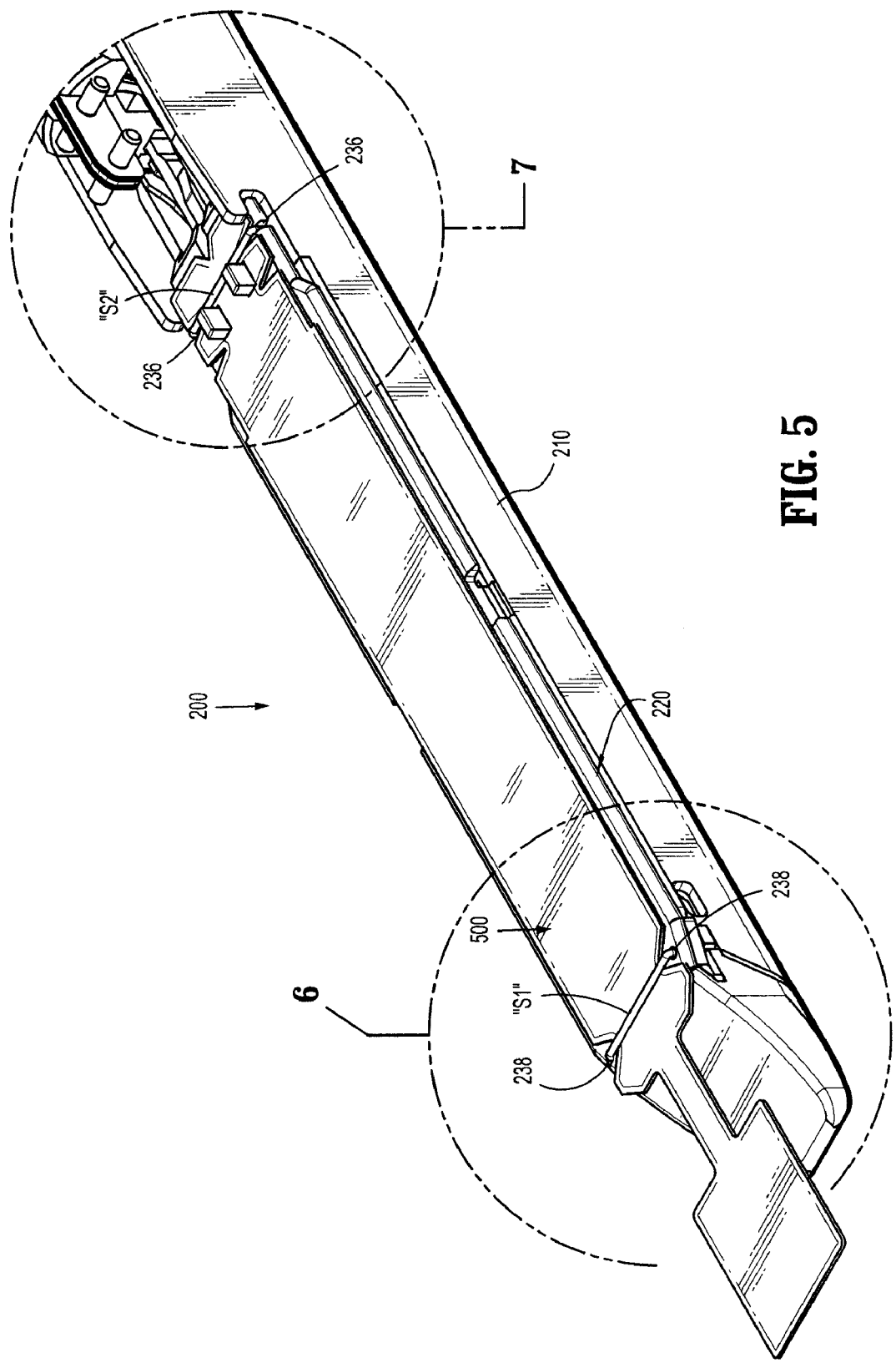
FIG. 5 is a perspective view of a cartridge assembly of the DLU of FIG. 2.
Figure 6:
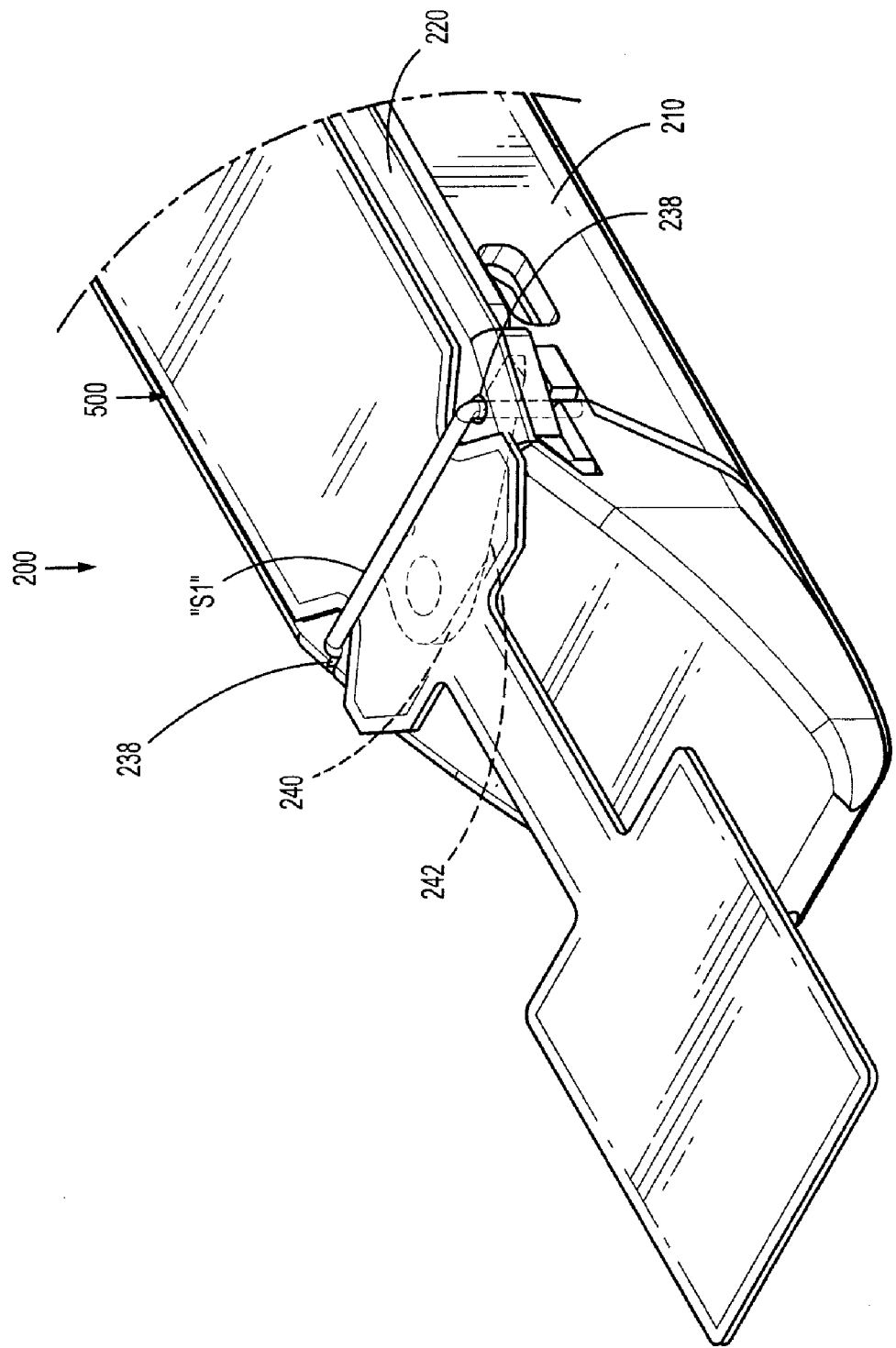
FIG. 6 is an enlarged perspective view of a distal end of the cartridge assembly of FIG. 5.
Figure 7:
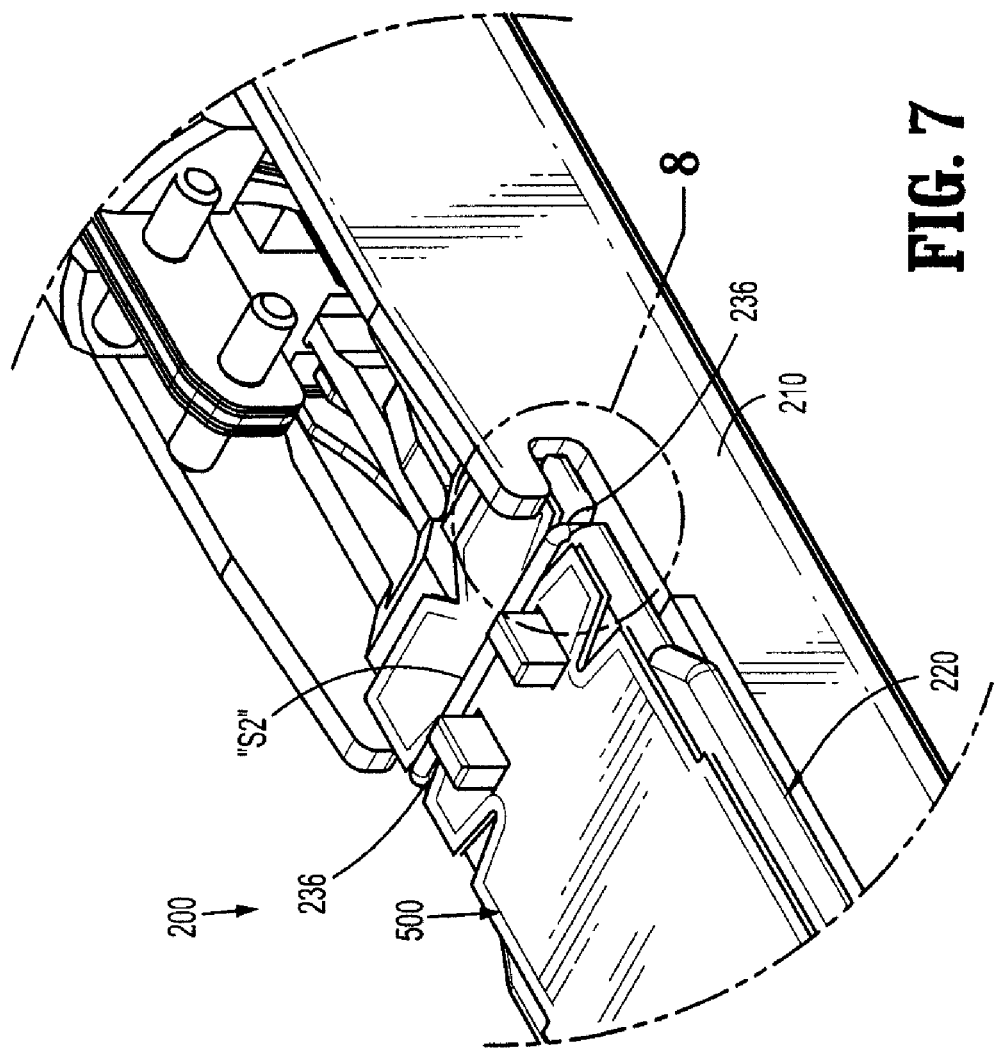
FIG. 7 is an enlarged view of the indicated area of detail of FIG. 5.
Figure 8:
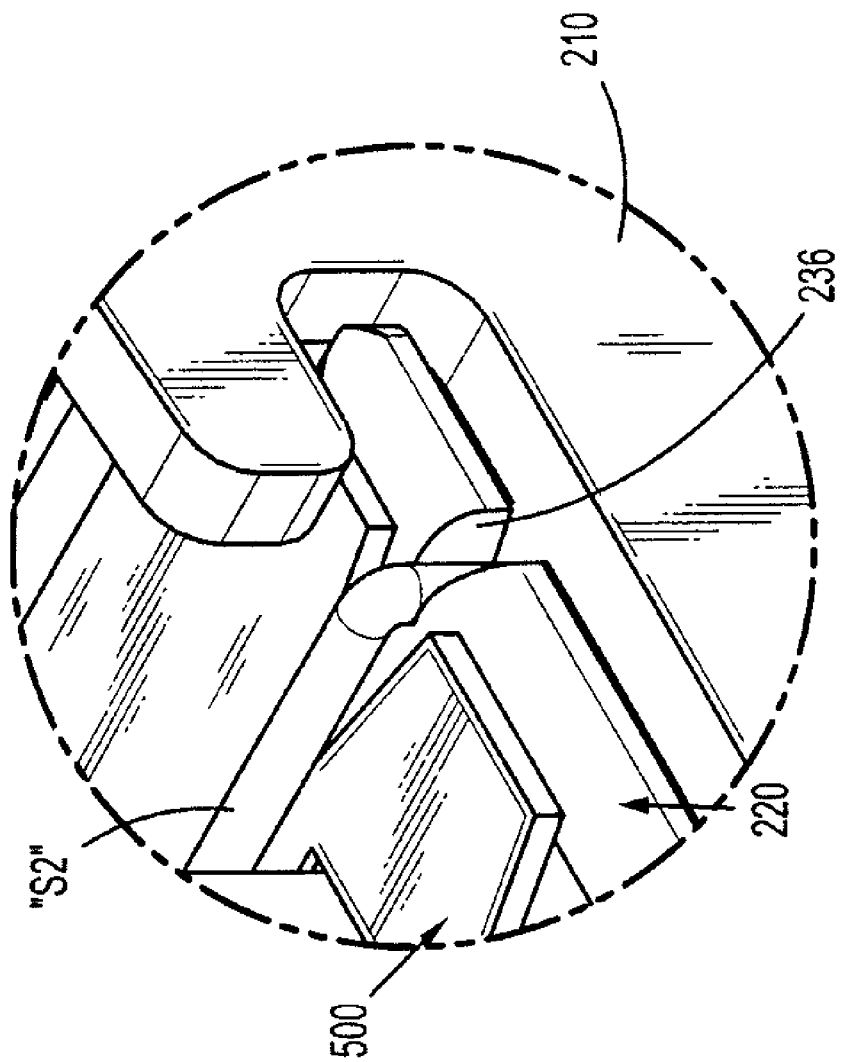
FIG. 8 is an enlarged view of the indicated area of detail of FIG. 7.

With reference to FIG. 3, an embodiment of a surgical buttress 500 having a uniform profile in accordance with the present disclosure, is illustrated. Buttress 500 includes a head portion 510, a body portion 520, and a neck portion 530 interconnecting head portion 510 and body portion 520.

Buttress 500 is configured to be detachably secured to any sized anvil assembly 300 and/or cartridge assembly 200, as described above. Body portion 520 of buttress 500 defines a pair of opposing distal recesses 524 on transverse edges near a distal location 522 thereof. The pair of opposing distal recesses 524 may be utilized to secure body portion 520 to a distal end of anvil assembly 300 and/or cartridge assembly 200, either through a use of suture "S1 or S3" or any other type of fastener, e.g., staple. Distal portion 522 of body portion 520 has a reduced transverse cross-sectional dimension, e.g., angled, arcuated, so as to be suitable for various types of anvil and cartridge assemblies having different shapes.

Body portion 520 of buttress 500 further defines two pairs of opposing proximal recesses 526a, 526b formed near a proximal end thereof. Each of the pair of proximal recesses 526a, 526b is disposed on a transverse side of body portion 520 near the proximal edge thereof. Such proximal recesses 526a, 526b serve to detachably secure buttress 500 to a proximal end of anvil assembly 300 and/or cartridge assembly 200. In order to accommodate various types of profiles, body portion 520 of buttress 500 preferably has been provided with two pairs of opposing recesses, a first proximal pair 526a, and a second proximal pair 526b (located distal of the first proximal pair 526a). Each of the proximal pair of recesses 526a, 526b has a substantially v-shape profile, although other shapes are contemplated.

In particular, when buttress 500 is to be used with a relatively longer anvil assembly 300 and/or cartridge assembly 200, then a suture "S2 or S4" is extended across a proximal end of body portion 520 of buttress 500, passed through the proximal-most pair of recesses 526a of buttress 500, and secured to respective recesses 316 of anvil assembly 300 and/or recesses 236 of cartridge assembly 200. Moreover, when buttress 500 is to be used with a relatively shorter anvil assembly 300 and/or cartridge assembly 200, then a suture "S2 or S4" is extended across a proximal end of body portion 520 of buttress 500, passed through the distal pair 526b of the proximal pair of recesses of buttress 500, and secured to respective recess 316 of anvil assembly 300 and/or recesses 236 of cartridge assembly 200.

According to another aspect of the present disclosure, a single profile or configuration buttress 500 may be used in connection with cartridge assembly 200 and/or anvil assembly 300. For example, the buttresses 500 that are used in connection with cartridge assembly 200 and anvil assembly 300 each may have the same overall length, width, thickness, perimetrical profile and material of construction.

In particular, as seen in FIG. 10, when buttress 500 is used in connection with cartridge assembly 200, a suture "S1" may extend transversely across a distal end portion of cartridge assembly 200 and be captured by or otherwise be secured to distal pair of recesses or attachment points 238 of cartridge assembly 200, wherein suture "S1" is in registration with distal recesses 524 of secure body portion 520 of buttress 500. Additionally, when buttress 500 is used in connection with cartridge assembly 200, a suture "S2" may extend transversely across a proximal end portion of cartridge assembly 200 and be captured by or otherwise secured to each of a proximal pair of recesses or attachment points 236 of cartridge assembly 200, wherein suture "S2" is in registration with the proximal-most pair 526a of the proximal pair of recesses of body portion 520 of buttress 500.

With continued reference to FIG. 10, when buttress 500 is used in connection with anvil assembly 300, a suture "S3" may extend transversely across a distal end portion of anvil assembly 300 and be captured by or otherwise secured to the distal pair of recesses or attachment points 318 of anvil assembly 300, wherein suture "S3" is in registration with distal recesses 524 of secure body portion 520 of buttress 500. Additionally, when buttress 500 is used in connection with anvil assembly 300, a suture "S4" may extend transversely across a proximal end portion of anvil assembly 300 and be captured by or otherwise secured to each of a proximal pair of recesses or attachment points 316 of anvil assembly 300, wherein suture "S4" is in registration with the distal pair 526b of the proximal pair of recesses of body portion 520 of buttress 500.

Neck portion 530 connects head portion 510 to a distal end of body portion 520. Generally, head portion 510 is in a substantially rectangular shape which is used as a tab to facilitate placement of buttress 500 in position on anvil assembly 300 and/or cartridge assembly 200. Following placement of buttress 500 on anvil assembly 300 and/or cartridge assembly 200, head portion 510 and neck portion 530 may be torn or otherwise cut away from body portion 520. The neck portion may have perforations for this purpose, in certain embodiments.

Body portion 520 further includes a notch 528 at a proximal edge thereof. Notch 528 is substantially centered with respect to the longitudinal axis. Notch 528 which has a triangular or V-shape configuration (although other shapes are contemplated) may be utilized to provide a lead-in for the knife during a cutting of surgical cartridge buttress 500.

The uniform profile of buttress 500 which simultaneously satisfies the requirements of one or more different assemblies offers advantages of simplifying the assembly process, minimizing the total number of unique components, and reducing assembly costs associated therewith.

Moreover, buttress 500 may be used on or in connection with cartridge assembly 200 and/or anvil assembly 300. In this manner, a single profile buttress 500 is produced and used for cartridge assembly 200 and/or anvil assembly 300. As such, the manufacturing and storage costs for buttresses 500 may be reduced.

As mentioned above, DLU 100 includes an anvil surgical buttress 500 and a cartridge surgical buttress 500 pre-loaded onto anvil assembly 300 and cartridge assembly 200. An exemplary method of loading anvil assembly 300 and/or cartridge assembly 200 with a buttress 500 will now be described.

During the manufacturing and/or assembly process of DLU 100, loading of anvil assembly 300 and/or cartridge assembly 200 with buttress 500 includes placing a buttress 500 atop a tissue contacting surface of anvil assembly 300 and/or cartridge assembly 200 such that notch 528 of buttress is disposed near a proximal end of anvil assembly 300 and/or cartridge assembly 200 and head portion 510 of buttress 500 extends from a distal end of anvil assembly 300 and/or cartridge assembly 200. With buttress 500 so positioned against anvil assembly 300 and/or cartridge assembly 200, proximal sutures "S2" and/or "S4" are pulled down. Tension is then applied to buttress 500, in a distal direction, by pulling on head portion 510. Distal sutures "S1" and/or "S3" are then pulled down. At this time, all the sutures "S1-S4" are cinched in the respective attachment points 316, 318, 236, 238 of anvil assembly 300 and/or cartridge assembly 200. Following cinching of sutures "S1-S4," head portion 510 of buttress 500 may be released. Next, DLU 100 may be removed from a nesting and head portion 510 and neck portion 530 of buttress 500 may be removed or severed from body portion 520.

The present disclosure also contemplates a method of forming the buttress. The buttress is formed from a suitable biocompatible or biocompatible and bioabsorbable material. In certain preferred embodiments, the buttresses are each fabricated from a non-absorbent material which does not retain fluid. The buttresses, in certain embodiments, are each fabricated from "BIOSYN" made from GLYCOMER 631 (a block copolymer), a synthetic polyester composed of glycolide, dioxanone and trimethylene carbonate.

One block of the resulting copolymer contains randomly combined units derived from p-dioxanone (1,4-dioxan-2-one) and trimethylene carbonate (1,3-dioxan-2-one). The second block of the copolymer contains randomly combined units derived from glycolide and p-dioxanone. The resulting polyester is an ABA triblock terpolymer possessing about 60% glycolide, about 14% dioxanone, and about 26% trimethylene carbonate.

Exemplary surgical buttresses "B" for use with the surgical stapling devices disclosed herein are shown and described in commonly assigned U.S. Pat. Nos. 5,542,594; 5,908,427; 5,964,774; and 6,045,560, and commonly assigned U.S. Application Serial Nos. 2006/0085034, filed on Apr. 20, 2006; and 2006/0135992, filed on Jun. 22, 2006, the entire contents of each of which is incorporated herein by reference.

The shape of the buttress may be formed by forming a sheet of the biocompatible material and cutting the desired shape into the sheet. The buttress may also be molded in the desired shape. In certain embodiments, a sheet of the biocompatible material is formed and then the profile or shape is cut off the sheet using roller die sets. A method of forming the buttress can follow these steps: a sheet of buttress material is fed through one side of a tool; the tool has the roller die sets with the exact desired profiles on it; the die sets stamp the exact profile on the sheet of buttress material; the profile is still loosely connected to the sheet of buttress material so that the sheet of buttress material comes out of the tool from a second side. The buttresses with the desired profiles are then pulled off the sheet of buttress material, which can be done manually.

While the above-described embodiments surgical staplers incorporating the use of movable knife blades to sever and release surgical buttresses from the tissue contacting surfaces of the anvil assembly and the cartridge assembly have been shown and described in relation to endoscopic surgical staplers, it is envisioned and within the scope of the present disclosure that any of the above-embodiments may be incorporated into any type of surgical stapler, including and not limited to open surgical staplers, such as, for example, linear surgical staplers and transverse surgical staplers.

Moreover, while only distal and proximal sutures have been shown and described as securing buttress 500 to anvil assembly 300 and/or cartridge assembly 300, it is contemplated that any number of transverse sutures may be provided along a length of the anvil assembly and/or cartridge assembly to aid with the securement of buttress 500 along a length thereof.

It will be understood that various modifications may be made to the embodiments disclosed herein. For example, the stapling apparatus need not apply staples but rather may apply two part fasteners as is known in the art. Further, the length of the linear row of staples or fasteners may be modified to meet the requirements of a particular surgical procedure. Thus, the length of a single stroke of the actuation shaft and/or the length of the linear row of staples and/or fasteners within a disposable loading unit may be varied accordingly. Therefore, the above description should not be construed as limiting, but merely as exemplifications of preferred embodiments. Those skilled in the art will envision other modifications within the scope and spirit of the claims appended thereto.

What is claimed is:

1. A surgical stapling apparatus, comprising:
    a cartridge assembly defining a first tissue contacting surface, the cartridge assembly housing a plurality of surgical fasteners therein, the cartridge assembly defining at least one distal attachment point and at least one proximal attachment point;
    an anvil assembly defining a second tissue contacting surface, the anvil assembly movably secured in relation to cartridge assembly, the anvil assembly defining at least one distal attachment point and at least one proximal attachment point, wherein the at least one proximal attachment point of the anvil assembly is offset an axial distance from the at least one proximal attachment point of the cartridge assembly; and
    a surgical buttress releasably secured to each of the first tissue contacting surface and the second tissue contacting surface, the surgical buttress including a body portion configured to substantially overlie at least one of the first and second tissue contacting surfaces of either the first length and second length cartridge assembly and anvil assembly;

wherein each surgical buttress defines a distal attachment feature for registration with the distal attachment point of the cartridge assembly and the anvil assembly;

wherein each surgical buttress defines a first proximal attachment feature and a second proximal attachment feature offset an axial distance from the first proximal attachment feature;

wherein the first proximal attachment feature registers with the proximal attachment point of the cartridge assembly; and wherein the second proximal attachment feature registers with the proximal attachment point of the anvil assembly.

2. The surgical stapling apparatus of claim 1, wherein the surgical buttress disposed against the tissue contact surface of the cartridge assembly and the surgical buttress disposed against the tissue contact surface of the anvil assembly have substantially the same length.

3. The surgical stapling apparatus of claim 1, wherein each surgical buttress has the same configuration.

4. The surgical stapling apparatus of claim 1, wherein each surgical buttress is fabricated from a biocompatible and bioabsorbable material.

5. The surgical stapling apparatus of claim 1, further comprising sutures retaining surgical buttresses against the tissue contacting surface of the cartridge assembly and the anvil assembly.

6. The surgical stapling apparatus of claim 1, further comprising a suture retaining a distal end portion of the surgical buttress against a respective one of the cartridge assembly and the anvil assembly, wherein the suture maintains the distal attachment feature of the surgical buttress in registration with the distal attachment point of the respective one of the cartridge assembly and the anvil assembly.

7. The surgical stapling apparatus of claim 1, further comprising a suture retaining a proximal end portion of the surgical buttress against a respective one of the cartridge assembly and the anvil assembly, wherein a suture maintains the first proximal attachment feature of the surgical buttress in registration with the proximal attachment point of the cartridge assembly and the anvil assembly, and wherein a suture maintains the second proximal attachment feature of the surgical buttress in registration with the proximal attachment point of the anvil assembly.

8. A surgical stapling apparatus, comprising:
a cartridge assembly defining a first tissue contacting surface, the cartridge assembly housing a plurality of surgical fasteners therein, the cartridge assembly being either a first length or a second length longer than the first length;
an anvil assembly defining a second tissue contacting surface, the anvil assembly movably secured in relation to cartridge assembly, the anvil assembly being either the first length or the second length each corresponding to the length of the cartridge assembly; and
a surgical buttress releasably secured to at least one of the first tissue contacting surface and the second tissue contacting surface, the surgical buttress including a head portion, a neck portion, and a body portion, wherein the head portion is connected to a distal end of the body portion by the neck portion, wherein the surgical buttress is configured to substantially overlie at least one of the first and second tissue contacting surfaces of either the first length and second length cartridge assembly and anvil assembly.

9. The surgical stapling apparatus of claim 8, wherein the body portion of the surgical buttress defines a recess formed in a proximal edge thereof, the recess longitudinally bisecting the proximal edge.

10. The surgical stapling apparatus of claim 9, wherein the recess is a notch having a v-shape profile.

11. The surgical stapling apparatus of claim 8, wherein the body portion of the surgical buttress defines at least one pair of opposing proximal recesses, each of the at least one pair of opposing proximal recesses is formed on an opposing lateral side of the body portion near a proximal edge of the surgical buttress.

12. The surgical stapling apparatus of claim 11, wherein the at least one pair of opposing proximal recesses is a notch having a v-shape profile.

13. The surgical stapling apparatus of claim 11, wherein the body portion of the surgical buttress further defines a pair of opposing distal recesses, each of the pair of opposing distal recesses is formed on an opposing lateral side of the body portion near a distal edge of the body portion.

14. The surgical stapling apparatus of claim 13, wherein the pair of opposing distal recesses are longitudinally tapered.

15. The surgical stapling apparatus of claim 8, wherein a distal edge of the body portion of the surgical buttress is arcuated.

16. The surgical stapling apparatus of claim 8, wherein a distal edge of the body portion of the surgical buttress has a transverse width dimension less than that of the rest of the body portion.

17. The surgical stapling apparatus of claim 8, wherein the head portion has a substantially rectangular shape.

18. The surgical stapling apparatus of claim 8, wherein each surgical buttress is fabricated from a biocompatible and bioabsorbable material.

19. A surgical buttress for use in a surgical stapling apparatus, the surgical buttress comprising:
a body portion;
a neck portion; and
a head portion connected to a distal end of the body portion by the neck portion, wherein the body portion defines at least one pair of opposing proximal recesses, each of the at least one pair of opposing proximal recesses is formed on an opposing lateral side of the body portion near a proximal edge of the body portion.

20. The surgical buttress of claim 19, wherein each of the at least one pair of opposing proximal recesses is a notch having a v-shape profile.

21. The surgical buttress of claim 19, wherein the body portion further defines a pair of opposing distal recesses, each of the pair of opposing distal recesses is formed on an opposing lateral side of the body portion near a distal edge of the body portion.

22. The surgical buttress of claim 19, wherein the body portion of the surgical buttress further defines a proximal edge recess formed in a proximal edge thereof, the proximal edge recess longitudinally bisecting the proximal edge.

23. The surgical buttress of claim 19, wherein a distal edge of the body portion of the surgical buttress is arcuated.

24. The surgical buttress of claim 19, wherein a distal edge of the body portion of the surgical buttress has a transverse width dimension less than that of the rest of the body portion.

25. The surgical buttress of claim 19, wherein the head portion has a substantially rectangular shape.

26. The surgical buttress of claim 19, wherein the surgical buttress is fabricated from a biocompatible and bioabsorbable material.

27. A surgical buttress for use with a surgical stapling apparatus having a cartridge assembly of any number of lengths and an anvil assembly of any number of lengths corresponding to the lengths of the cartridge assembly, wherein each of the cartridge assembly and anvil assembly defines respective juxtaposed tissue contacting surfaces, and wherein the cartridge assembly includes a plurality of staples stored in staple slots thereof for formation against staple formation pockets of the anvil assembly, the surgical buttress comprising:
  a body portion configured and dimensioned to at least one of:
    overlie all of the staple slots of the cartridge assembly for any length cartridge assembly, and
    overlie all of the staple formation pockets of the anvil assembly for any length anvil assembly;
  a neck portion extending from the body portion; and
  a head portion connected to the neck portion and opposite a distal end of the body portion, wherein the body portion defines at least one pair of opposing proximal recesses, each of the at least one pair of opposing proximal recesses is formed on an opposing lateral side of the body portion near a proximal edge of the body portion.

* * * * *